(12) United States Patent
Highsmith

(10) Patent No.: US 6,423,667 B1
(45) Date of Patent: Jul. 23, 2002

(54) AMMONIUM SULFATE SUSPENSIONS IN OILS

(75) Inventor: Ronald Earl Highsmith, Chesterfield, VA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/855,481

(22) Filed: May 15, 2001

(51) Int. Cl.[7] .......................... A01N 25/22; C05C 3/00; B01F 3/12
(52) U.S. Cl. ...................... 504/362; 71/63; 510/33
(58) Field of Search ............................. 504/362; 71/63; 516/33

(56) References Cited

U.S. PATENT DOCUMENTS

| | | | |
|---|---|---|---|
| 3,317,635 A | 5/1967 | Osmond et al. | 260/881 |
| 3,793,015 A | 2/1974 | Van Engeland et al. | 430/112 |
| 4,393,151 A | 7/1983 | Dawans et al. | 523/130 |
| 4,966,728 A | 10/1990 | Hazen | 252/354 |
| 5,135,561 A | 8/1992 | Boles | 71/28 |
| 5,439,497 A | 8/1995 | Boles | 71/63 |
| 5,521,144 A | 5/1996 | Farr et al. | 504/215 |
| 5,658,855 A | 8/1997 | Nalewaja et al. | 504/214 |
| 5,707,551 A * | 1/1998 | Pallas et al. | 252/308 |
| 6,030,923 A | 2/2000 | Okano et al. | 504/116 |
| 6,165,939 A | 12/2000 | Agbaje et al. | 504/105 |

FOREIGN PATENT DOCUMENTS

| | | | |
|---|---|---|---|
| GB | 1151141 | 5/1969 | |
| WO | WO 99/12869 | 3/1999 | C05G/3/00 |

OTHER PUBLICATIONS

U. Suwunnamek et al., "Control of *Cyjperus rotudu* with glyphosate. Influence of ammonium sulfate and other additives", *Weed Research*, 15 13–19 (1975).

H. De Ruiter et al., "The Influence of Different Adjuvants on the Phytotoxicity of glyphosate and fluazifop–p–butyl", *Landbouwwet*, 52(3B), 1217–24 (1987).

Y. Yan et al., "Rheology of Oil–in Water Emulsions with Added Solids", *Chem. Eng. Sci.* 46 (4), 985–994 (19910.

R.M. Turian, "Characterization, settling, and rheology of concentrate fine particulate mineral slurries", *Powder Technology*, 93, 219–223 (1997).

Kirk–Othmer Encyclopedia of Chemical Technology, Second Ed., vol. 8, 128–137, John Wiley & Sons, New York, 1965.

* cited by examiner

*Primary Examiner*—S. Mark Clardy
(74) *Attorney, Agent, or Firm*—Melanie L. Brown; Virgina Szigeti; Margaret Millikin

(57) ABSTRACT

Stable concentrated suspensions readily dispersible in water comprising ammonium sulfate, a surfactant, and an oil. The ammonium sulfate particles are at least about 99 wt. % passable through a Tyler #48 sieve. The surfactant has an HLB rating from about 10 to about 15. The oil is a hydrocarbon or other non-polar oil having a viscosity of at least about 5 centipoises at 40° C. The ammonium sulfate suspensions of the invention are useful as herbicidal adjuvants, herbicidal compositions or for other purposes.

20 Claims, 2 Drawing Sheets

Figure 2
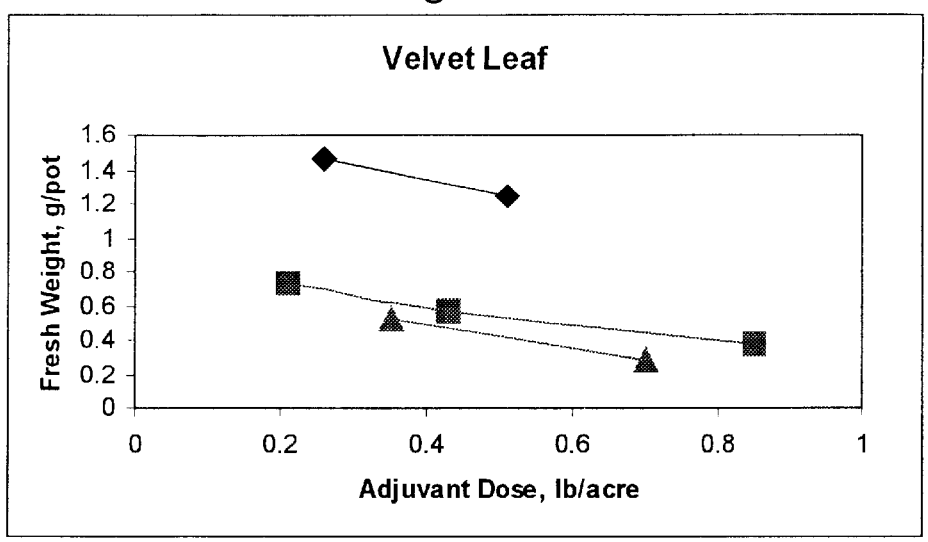
Fig. 2A
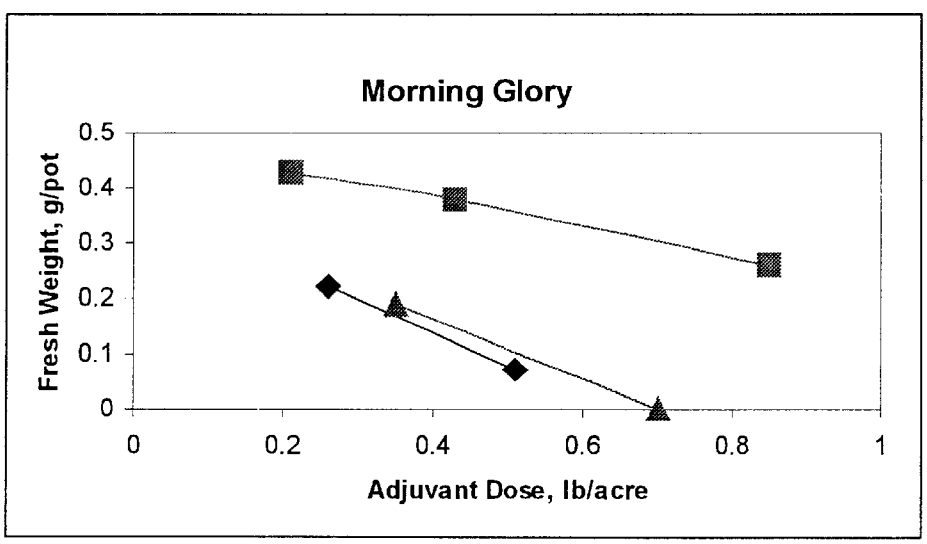
Fig. 2B
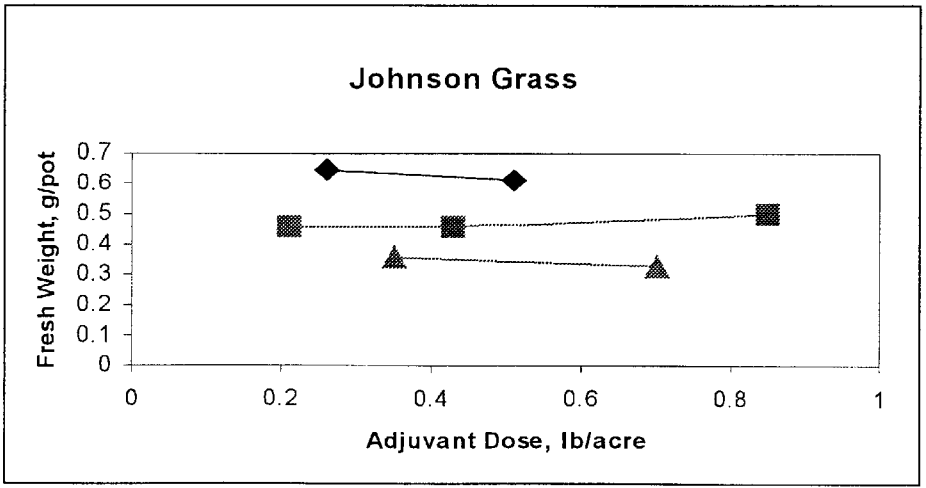
Fig. 2C

AMMONIUM SULFATE SUSPENSIONS IN OILS

AMMONIUM SULFATE SUSPENSIONS IN OILS

Background of the Invention

1. Field of the Invention

The present invention relates to high concentration ammonium sulfate suspensions in oil that exhibit acceptable physical stability during normal storage conditions, and that upon dilution in a suitable volume of water, are suitable for application to plants as herbicidal compositions, adjuvants in herbicidal compositions, or fertilizers, or that may be used for other purposes.

2. Description of the Related Art

When growing crops in a field, it is important to kill or control the growth of undesirable plants (weeds) in the field. If not controlled, the weeds compete with crop plants for essential resources such as soil nutrients, water and sunlight. By removing a fraction of the resources or otherwise reducing the availability of these resources to crop plants, the weeds restrict crop growth, resulting in loss of crop yield.

Timely and judicious use of herbicides can provide weed control to minimize crop losses and production costs. Herbicides such as glyphosate (N-phosphonomethyl glycine) and many others are useful for control of a large variety of weeds. When used in an herbicidal composition, glyphosate is generally in the form of one of its various salts in solution, preferably an aqueous solution.

Adjuvants are materials that enhance the action of herbicides by promoting adsorption and translocation and by complexing antagonistic metal ions in the water used to make the herbicide solution. Ammonium sulfate has been known as an adjuvant. for several decades (U. Suwunnamek and D Penner, *Weed Research*, 15, 13–19 (1975)). It is perhaps the most important commercial adjuvant and is also widely used as a fertilizer. Several different types of oils have also been found to act as adjuvants. However, mineral oil has been reported to decrease the activity of glyphosate herbicide (H. De Ruiter et al., Cent. Agrobiol. Res., Wageningen, Neth., Meded. Fac., *Landbouwwet, Rijksuniv. Gent*, 52(3B) 1217–24 (1987)).

Herbicides are typically applied to field crops by spraying an aqueous mixture of several components. Polymers that inhibit spray drift, defoamers, and other chemicals that enhance the performance of an herbicide are sometimes mixed with the ammonium sulfate. All solid components of a mixture are typically ground to a small particle size in order to reduce the time required to dissolve. Growers and contract applicators use a "mix" tank to prepare the herbicide mixture. A typical mix consists of about 800 pounds of water, 8 to 17 pounds of herbicide, and 8 to 17 pounds of dry adjuvant. The result is a 1% or 2% solution of herbicide and 1% or 2% of adjuvant. The typical tank has relatively poor mixing and the applicator, whether using a truck or airplane, usually has little time to wait for dissolution. Even small particles tend to fall to the bottom of the mix tank in clumps and are sometimes slow to dissolve. In addition, these dry adjuvants generate undesirable dusty conditions when the package is opened and poured into the mix tank. Therefore, liquid preparations are preferable.

However, many liquids suffer disadvantages because of low product concentration. Freight, handling, and packaging costs become a substantial part of the total product cost. It would be desirable to have ammonium sulfate in a high concentration liquid form, but because storage temperature conditions vary, the highest practical concentration of ammonium sulfate in aqueous solution is about 38%. Water is the only practical solvent because ammonium sulfate is practically insoluble in all other common solvents. Thus, while aqueous solutions are not satisfactory, there remains a need for a liquid ammonium sulfate product.

Another approach to preparing a liquid product is to make a suspension. However, in aqueous suspensions of ammonium sulfate, crystal dissolution and recrystallization occurs continually. This results in a progressive increase of the size of the particles and eventual settling.

U.S. Pat. No. 5,135,561 describes aqueous suspensions produced by mixing ammonium sulfate with ammonia and clay. U.S. Pat. No. 6,030,923 describes aqueous agricultural compositions optionally containing ammonium sulfate at concentrations up to 40 wt. %. U.S. Pat. No. 6,165,939 describes "suspensoemulsions" optionally containing ammonium sulfate dissolved in the aqueous phase. U.S. Pat. No. 5,658,855 discloses aqueous herbicidal adjuvants optionally containing ammonium sulfate at concentrations up to 50 wt. %. U.S. Pat. No. 5,707,551 describes suspensions of water-soluble solids in water miscible (polar) liquids.

There appears to be no previous report of ammonium sulfate suspensions in hydrocarbons or non-polar oils. The literature on suspensions in hydrocarbon or other non-polar liquids is sparse. U.S. Pat. No. 3,793,015 and British patent GB 1151141 reported stable suspensions of particles such as carbon black in aliphatic hydrocarbons using metal salts of pyrophosphates and similar agents as dispersing agents. U.S. Pat. No. 3,317,635 described dispersions of polymer particles in organic liquids. U.S. Pat. No. 4,393,151 described suspensions of water-soluble polymers in a liquid hydrocarbon medium including a thickening agent.

There is little understanding of the fundamentals of suspensions. For instance, Yan et. al. state that, "the effect of particle size on the rheology of suspensions is a controversial subject" (Y. Yan, et. al., *Chem, Eng. Sci.*, 46(4), 985–994, (1991)). Other authors have claimed that the shape and ionic character of the particles can be important factors. For instance, R. M. Turian, et. al. in a paper published in *Powder Technology*, 93, 219–223 (1997) suggests that the "interparticle interaction effects were quite strong" for the suspensions he investigated. Therefore it is to be expected that different particles may present uniquely different properties.

Surfactants and soluble polymers are often used to stabilize suspensions of particles. These may function by adsorption on the particle surface and may provide steric interference which inhibits settling. However, the interaction between a particular liquid, particle, and surfactant is impossible to predict.

The liquid in an ammonium sulfate suspension intended for agricultural purposes must comply with government regulations, and should be qualified for use with pesticides under the Code of Federal Regulations (CFR). Mineral oils and a few other oils such as soybean oil are listed in 40 CFR 180.1001 paragraph c and have been used as adjuvants themselves. Petroleum distillates are also approved under this section of the CFR provided they conform to the conditions of 21 CFR 172.882 or 21 CFR 172.884.

Once a stable concentrated ammonium sulfate suspension is achieved, it can be useful for agricultural use only if it dissolves in water fairly quickly. It is known in the surfactant art that a hydrophilic surfactant is needed to break up and disperse oil in water but there are hundreds of different types. The hydrophilic character of a surfactant is measured by a hydrophile-lipophile balance (HLB) scale (See for example: Kirk-Othmer *Encyclopedia of Chemical Technology, Second Edition*, 8, 128–137, (1965)). Surfactants with a high HLB rating are hydrophilic or "water-loving". Lower HLB surfactants are hydrophobic or oleophilic.

Very small particles of colloidal dimensions form stable suspensions even in dilute concentrations where hindered settling is not a factor. Colloidal particles are usually considered to be 0.001 mm (1 x micron) or less in diameter and form stable suspensions because of Brownian motion. However, the energy required to break down ammonium sulfate and most other materials to colloidal dimensions is extremely high and costly.

In the case of ammonium sulfate, there is a long-standing need to provide a low cost system that can form stable concentrated suspensions that are readily dispersible in water for use in agriculture and for other purposes.

SUMMARY OF THE INVENTION

The invention provides stable concentrated suspensions comprising ammonium sulfate, a surfactant, and an oil. The ammonium sulfate particles are at least about 99 wt. % passable through a Tyler #48 sieve. The surfactant is a non-ionic surfactant with an HLB rating from about 10 to about 15. The oil is a hydrocarbon or other non-polar oil having a viscosity of at least about 5 centipoises (cp) at 40° C. The suspensions of the invention exhibit physical stability during normal storage conditions, and are readily dispersed in water.

In another embodiment, the ammonium sulfate suspensions of the invention additionally contain methylthio-α-hyroxybutyric acid. It is surprisingly found that methylthio-α-hyroxybutyric acid enhances the stability and reduces the viscosity of the ammonium sulfate suspensions of the invention.

In yet another embodiment, the ammonium sulfate suspensions of the invention additionally contain a solid herbicide.

Preferably, the suspensions of the invention, upon dilution in a suitable volume of water, are suitable for application to plants as herbicidal compositions, adjuvants in herbicidal compositions, or fertilizers, or may be used for other purposes. Weed-kill tests show that suspensions of the invention containing ammonium sulfate, mineral oil, and surfactant, diluted in water and in combination with an herbicide, exhibit synergistic effects in killing difficult weeds. Herbicide manufacturers usually recommend applying double the dose of herbicide when difficult weeds are present. However, from an environmental point of view it is more desirable to use less herbicide and an adjuvant to obtain the same effect. The suspensions of the invention meet that need.

Also and surprisingly, it has been found that the ammonium sulfate suspensions of the invention are compatible with water-soluble packaging whereas ammonium sulfate solids and aqueous solutions are not. This provides a distinct advantage in ease of use as the customer can drop a bag of pre-weighed chemicals into water without handling or measuring.

BRIEF DESCRIPTION OF THE DRAWINGS

In the accompanying drawing figures:

FIG. 2 shows plots of new growth (fresh weight) of weeds after application of herbicide-adjuvant compositions at doses less than 1 lb/acre.

FIG. 2A shows fresh weight of Velvet Leaf weed.

FIG. 2B shows fresh weight of Morning Glory weed.

FIG. 2C shows fresh weight of Johnson Grass weed.

DETAILED DESCRIPTION OF THE INVENTION

Figure 1:
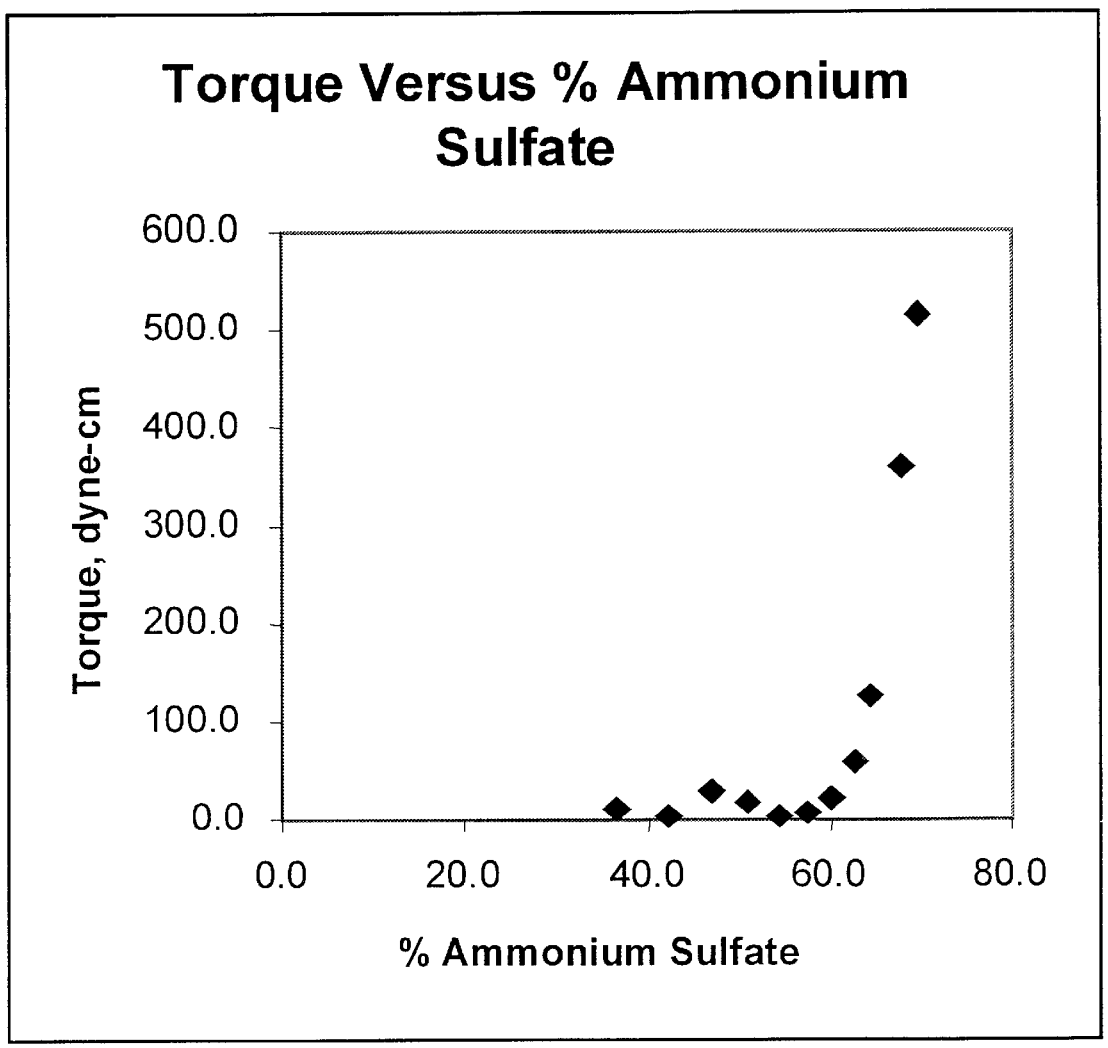
FIG. 1 shows a plot of viscometer torque versus the concentration of ammonium sulfate in mineral oil for several suspensions of the invention.

The products of the invention are stable concentrated suspensions of ammonium sulfate readily dispersible in water. Preferably, the suspensions, upon dilution in a suitable volume of water, are suitable for application to plants as herbicidal compositions, adjuvants in herbicidal compositions, or fertilizers, or may be used for other purposes.

An ammonium sulfate suspension of the invention is comprised of: ammonium sulfate particles more than about 99 wt. % passable through a Tyler #48 sieve; a non-ionic surfactant with an HLB rating between about 10 and about 15; and an non-polar oil having a viscosity of at least about 5 cp at 40° C. In the context of this invention, a non-polar oil is characterized by having a water solubility less than about 5 wt. % at 20° C.

In another embodiment, the ammonium sulfate suspensions of the invention also contain methylthio-α-hyroxybutyric acid.

In yet another embodiment, the ammonium sulfate suspensions of the invention additionally contain a solid herbicide.

In a preferred embodiment, the suspension of the invention is enclosed in a water-soluble container.

The invention is based on the discovery that ammonium sulfate, having particles within a certain size range, and in a concentration range, in combination with particular surfactants can form stable suspensions in non-polar liquids that -are readily dispersible in water and are useful products. This is a surprising result since it is found that other inorganic solid materials, similar to ammonium sulfate and having similar particle sizes, do not form stable suspensions in the same liquids. For the purposes of the invention a suspension is defined as stable if over a period of six months of storage at 23° C., less than about 5 wt % of the suspension separates into a free liquid phase. Preferably, a suspension of the invention shows no phase separation.

Generally, any ordinary ammonium sulfate that is commercially available and suitable for use as fertilizer may be used in the suspensions of this invention. One example of useful ammonium sulfate is commercially available from Honeywell International Inc. Preferably, the ammonium sulfate to be used in this invention is of at least about 95 wt % purity and contains less than about 0.2 wt % of water insoluble (filterable) organic or carbonaceous impurities. The filterable impurities are determined by dissolving 10 wt % of the ammonium sulfate in water at 23° C., then passing at least 50 g of the solution through a membrane filter of 0.45 micrometer opening size (e.g. Gelman Supor® brand filter). The organic and carbonaceous content as determined by combustion analysis of the dried filter cake should be less than about 0.2 wt % of the ammonium sulfate.

The particle size and particle size distribution of the ammonium sulfate are important to achieving the objectives of the invention. Generally, the smaller the particle the higher the viscosity and the better the stability of the suspensions. It is too costly to separate specific sizes of particles. It is desirable to be able to utilize the size distribution resulting from common grinding processes The suspensions of the invention have this advantage.

Suspension stability also increases with higher viscosity oils. Experiments in various hydrocarbon liquids having viscosities less than about 5 cp at 25° C. show that particles with an average diameter larger than about 0.30 mm in diameter settle rapidly. Different grinding processes can produce different size distributions even if all particles are less than 0.3 mm in diameter. A Tyler Number 48 sieve has an opening of 0.30 mm. Therefore, it is preferred that the ammonium sulfate particles used in the invention are substantially passable through a Tyler #48 sieve. It is additionally preferred that at least 8 wt. % of the ammonium sulfate particles pass a Tyler #230 sieve.

A most preferred particle size range for use with oils in the viscosity range of 5–30 cp at 40° C. is as follows:

| Tyler Sieve No. | Opening Size, mm | Weight % Retained on Sieve |
| --- | --- | --- |
| 48 | 0.30 | Less than 1 |
| 60 | 0.25 | 0–10 |
| 80 | 0.18 | 0–20 |
| 100 | 0.15 | 0–35 |
| 200 | 0.075 | 10–30 |
| 230 | 0.060 | 30–50 |
| 400 | 0.03 | 10–40 |
| pan | 0 | 10–20 |

This is representative of the size range produced by commercial ball milling of ammonium sulfate and requires no separation except substantial removal of particles retained by the Tyler #48 sieve. Smaller proportions of particles passing a Tyler #230 sieve may be used with oils of higher viscosity.

The concentration of ammonium sulfate in a suspension of the invention should be at least about 30 wt. %. It is preferred that the ammonium sulfate concentration be at least about 40 wt. %. More preferably, the ammonium sulfate concentration should be at least about 50wt. %.

Other solid materials of approximately the same particle size can also be incorporated in the suspensions of the invention, e.g., solid herbicides and drift-retardant polymers. These materials must not react with the other ingredients so as to make the suspension unstable. It is desirable to prepare a single product with all of these constituents. The additional particles can be ground with the ammonium sulfate or the suspension can be made and then the additional particles added to the suspension.

Petroleum distillates, corn oil, soybean oil, coconut oil, cotton seed oil and similar oils are suitable liquids for preparing the ammonium sulfate suspensions of the invention. The viscosity of the liquid should be at least about 5 centipoise (cp) and preferably at least about 10 cp at 40° C. Low viscosity (ca. 1 cp) petroleum fractions such as hexane and octane were not found suitable for preparing these suspensions. Medium viscosity distillates such as the commercially available Isopar® series by Exxon Chemical Co. enabled preparation of a suspension, but upon sitting for a few hours following agitation or stirring, separation of some free liquid was noted. The Isopar® series are primarily branched hydrocarbons with viscosities typically less than 3 cp.

Mineral oils or white oils are petroleum distillates from the heavy distillate fraction of crude petroleum. They are refined to remove the unsaturated hydrocarbons and improve oxidation stability. Mineral oil viscosities range from about 10 cp to about 220 cp at 40° C. Mineral oil is preferred to be used in the suspensions of the invention because it is consistent in quality, relatively low in cost, and readily available in a range of viscosities.

Cotton seed oil, corn oil, coconut oil, and soybean oil may also be used in the suspensions of the invention. Corn oil has a viscosity of about 200 cp at 25° C. Soybean oil is preferred over cottonseed oil and corn oil because it has one of the lowest costs. Soybean oil has a viscosity of about 80cp at 25° C. Epoxidized soybean oil is higher in cost but is more resistant to microbial degradation and may also be used. Other useful oils include petroleum oils, polyoxyethylated castor oil, cod liver oil, epoxidized linseed oil, fish oil, oils derived from plants and animals, mineral oil, sperm oil, tall oil, wintergreen oil, and rapeseed oil.

Oil soluble additives such as defoamers can be incorporated in the suspension in less than 5 wt % concentration. Oil soluble herbicides may also be added but only up to the point where oil properties are significantly degraded.

A characteristic of the suspensions of the invention is that they disperse rapidly upon dilution in water and the ammonium sulfate is quickly dissolved. Rapid dispersability of the oil-based suspensions in water is achieved by incorporation of a surfactant having an inverting effect. A preferred surfactant is a high HLB, non-ionic surfactant. Preferably, the HLB is between 10 and 15.

Preferably the surfactant is a non-ionic surfactant consisting of a polyethylene oxide-sorbitan fatty acid ester. Surfactants having 20 moles of poly(ethylene oxide) (POE) per mole with an oleate base are most preferred. Such surfactants are available from Imperial Chemical Industries through the Uniqema Division. A most preferred surfactant is POE (20) sorbitan trioloeate available from Uniqema as Tween® 85 having an HLB of 11.0. Surfactant concentrations of about 3 wt. % to about 8 wt. %% of the total mixture are preferred with about 4 wt. % to about 5 wt. % being more preferred. Higher surfactant concentrations have no or little adverse effect except increasing the cost. Normally such surfactants are not regarded as influencing the properties of the suspension, however it has been found that Tween® 85 surfactant produces a surprising decrease in the viscosity of the suspension. Rapid dispersion in water is aided by low suspension viscosity.

Surprisingly, It has been found that incorporation of about 0.03 to 2 wt. % of methylthio-α-hydroxybutyric acid (chemical formula: $CH_3SCH_2CH_2CH(OH)COOH$) further enhances the stability and further reduces the viscosity of the suspensions of the invention. Over one hundred other compounds had been screened for this purpose without success and there appears to be no prior art reference suggesting this functionality for methylthio-α-hydroxybutyric acid. The synthesis of methylthio-α-hydroxybutyric acid has been described in U.S. Pat. No. 2,745,745 hereby incorporated by reference to the extent not incompatible herewith. Methylthio-α-hydroxybutyric acid is an article of commerce sold as an animal feed supplement by Aventis Animal Nutrition, Alpharetta, Ga. in the form of an 88% aqueous solution under the tradename Rhodimet® AT-88.

The suspensions of the invention can be prepared by simple mixing of the ingredients provided that the particles of ammonium sulfate have been previously ground to the proper size. The mixing can be done by any of the well known methods for combining solids and liquids such as described in Perry's Chemical Engineers Handbook, Sixth Edition, P.19.5–19.24, McGraw Hill, New York, 1983. In some cases it may be desirable to grind or mill the ammonium sulfate in the oil but this choice is well known in the art of grinding. Any conventional means of providing uniform mixing is suitable such as pug mills, blenders, agitated tanks, and helical mixers. The order of introduction of the materials appears to not be important except it is generally preferred to add the inverting surfactant after all the other ingredients have been mixed together.

Also and surprisingly, it has been found that suspensions of the invention are compatible with water-soluble packaging whereas ammonium sulfate by itself is not compatible with water-soluble packaging. Water-soluble bags are usually manufactured from water-soluble polyvinyl acetate-polyvinyl alcohol film. It is common practice for some agricultural and other chemicals to be packaged in water-soluble bags for customer convenience. With the suspensions of the invention, the customer can drop a bag of pre-weighed chemicals in water without handling or measuring.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLE 1

Ammonium sulfate granules of approximately 1 mm average size are obtained from Rhone-Poulenc. The granules are 98 wt. % ammonium sulfate containing less than 0.1 wt. % of water insoluble carbonaceous impurities. Forty pounds of this material is ball milled at the Union Process Company, Akron, Ohio. The ammonium sulfate is charged to a size 1 S ball mill together with ¼ inch (6.35 mm) stainless steel balls and batch dry ground at 350 RPM for 55 minutes. Cooling water on the ball mill jacket maintains the batch temperature at about 23° C. At the completion of the ball milling, the ammonium sulfate is screened to remove substantially all particles not passable through a Tyler #48 screen. The particle size distribution of the screened material is as follows in Table I.

TABLE I

| Tyler Sieve No. | Opening size, mm | Wt.% Retained |
| --- | --- | --- |
| 48 | 0.30 | Less than 0.1 |
| 60 | 0.25 | 03 |
| 80 | 0.18 | 0.4 |
| 100 | 0.15 | 0.3 |
| 200 | 0.075 | 18 |
| 230 | 0.060 | 49 |
| 400 | 0.030 | 19 |
| Pan | 0 | 13 |

9.25 g (58.9 wt. %) of the screened ammonium sulfate is mixed with 5.75 g (36.6 wt. %) of white mineral oil (Chevron Superla®) 5) having a viscosity of about 29 cp at 40° C. and 0.70 g (4.5 wt. %) of polyoxyethylene (20) sorbitan trioleate surfactant having an HLB of 11.0 (Uniqema Tween® 85). The mixture is observed after 5 minutes with particular reference to any settling and possible appearance of a free liquid phase. The apparent viscosity of a suspension not exhibiting free liquid is characterized by a Brookfield DV-E viscometer with a LV-4 spindle at 2.5 rpm after stabilizing for 5 minutes at 25° C. The DV-E spindle is a straight cylinder having a diameter of 3.15 mm. The viscometer data is presented in terms of torque (dyne-cm). The properties of this mixture and the mixtures of Comparative Examples 2–16 below are reported in Table II. Any phase separated free oil is decanted and weighed

EXAMPLE 2 (Comparative)

9.25 g (58.9 wt. %) of the screened ammonium sulfate prepared in Example 1 is mixed with 5.75 g (36.6 wt. %) Isopar® M (Exxon Chemical) having a viscosity of 2.7 cp at 25° C. and 0.70 g (4.5 wt. %) of Tween® 85. The properties of this mixture are reported in Table II below.

EXAMPLES 3–16 (Comparative)

The following reagent grade materials are obtained from Fisher Scientific:

Ammonium carbonate

Ammonium oxalate

Ammonium phosphate (dibasic)

Sodium chloride

Sodium sulfate

Ammonium chloride

Calcium carbonate

These materials are ground with a mortar and pestle and screened to remove substantially all particles not passable through a Tyler #48 sieve. Mixtures are prepared containing 9.25 g of each of the screened materials with together with 5.75 g of either Superla® 5 white mineral oil (29 cp viscosity at 40° C.) or Isopar® M solvent (2.7 cp viscosity at 25° C.) and 0.70 g of Tween® 85. The properties of these mixtures are reported in Table II below.

TABLE II

| | | Mixture | | |
| --- | --- | --- | --- | --- |
| Example or Comparative Example No. | Solid | Suspending Liquid | Free Liquid, g | Viscometer Torque, Dyne-cm |
| 1 | Ammonium sulfate | Mineral oil | none | 39 |
| 2(Comp.) | Ammonium sulfate | Isopar ® M | about 0.2 | * |
| 3(Comp.) | Ammonium carbonate | Mineral oil | none | 281 |
| 4(Comp.) | Ammonium carbonate | Isopar ® M | about 0.2 | * |
| 5(Comp.) | Ammonium oxalate | mineral oil | 3.0 | * |
| 6(Comp.) | Ammonium oxalate | Isopar ® M | 3.5 | * |

TABLE II-continued

| Example or Comparative Example No. | Solid | Suspending Liquid | Mixture Free Liquid, g | Viscometer Torque, Dyne-cm |
|---|---|---|---|---|
| 7(Comp.) | Ammonium phosphate | mineral oil | 1.7 | * |
| 8(Comp.) | Ammonium phosphate | Isopar ® M | 2.3 | * |
| 9(Comp.) | Sodium chloride | mineral oil | 3.8 | * |
| 10(Comp.) | Sodium chloride | Isopar ® M | 4.2 | * |
| 11(Comp.) | Sodium sulfate | mineral oil | 4.5 | * |
| 12(Comp.) | Sodium sulfate | Isopar ® M | 5.6 | * |
| 13(Comp.) | Ammonium chloride | mineral oil | 3.0 | * |
| 14(Comp.) | Ammonium chloride | Isopar ® M | 3.3 | * |
| 15(Comp.) | Calcium carbonate** | mineral oil | 1.0 | * |
| 16(Comp.) | Calcium carbonate** | Isopar ® M | 1.4 | * |

*Viscosity is not determined because of separation and inhomogenity.
**Calcium carbonate mixtures show copious sediment.

It is seen from Table II that ammonium sulfate has unusual and unexpected properties. It yields lower viscosity and higher stability mixtures than the other solids. Ammonium carbonate seemly shows similar stability. However, on closer examination of the ammonium carbonate suspension, it is found that almost all the solids have settled to the bottom of the container, leaving a dilute suspension at the top. This results in an unfavorably higher viscosity. Ammonium carbonate is also not useful as an adjuvant.

The Isopar® M mixtures show lower initial stability than did the mineral oil mixtures. Further, after sitting for several hours and then being stirred or agitated, the Isopar® M mixtures show additional phase separation, whereas the mineral oil mixtures do not.

The suspension of the invention (Example 1) is stored at 23° C. and examined periodically for the presence of free liquid over a six month period. No phase separation (free liquid) is observed over this period.

EXAMPLES 17–19 AND COMPARATIVE EXAMPLE 20

Ammonium sulfate is obtained from several sources as coarse materials (approximately 1 mm average size) and having differing degrees of purity. Each sample is milled in a SPEX 8000 ball mill manufactured by SPEX Industries, Edison, N.J. using two stainless steel ⅜ inch diameter balls for 15 minutes. The milled material is screened to remove substantially all particles retained on a Tyler #48 sieve. The typical particle size distribution of the screened materials is shown in Table III.

TABLE III

| Tyler Sieve No. | Opening size, mm | Wt.% Retained |
|---|---|---|
| 48 | 0.30 | Less than 0.1 |
| 60 | 0.25 | 6 |
| 80 | 0.18 | 15 |
| 100 | 0.15 | 31 |
| 200 | 0.075 | 13 |
| 230 | 0.060 | 0 |
| 400 | 0.030 | 19 |
| Pan | 0 | 15 |

Suspensions are prepared by mixing 9.25 g of each ammonium sulfate with 5.75 g of Superla® 5 white mineral oil described in Example 1 and 0.70 g of Tween® 85 surfactant described in Example 1. The samples are allowed to stand for four hours and then are remixed. Five days later, if phase separation has occurred, the free oil is decanted and weighed. Experience has shown that suspensions that are stable for several days are stable for periods exceeding six months. The ammonium sulfate sources, purity and free oil separated from each suspension are shown in Table IV.

TABLE IV

| Example or Comparative Example No. | Ammonium sulfate Source | Purity, wt. % | Water-Insoluble Carbonaceous Impurities, Wt % | Free Oil Separated from Suspension, g |
|---|---|---|---|---|
| 17 | AlliedSignal - RP | 98+ | Less than 0.1 | 0 |
| 18 | DSM | 95+ | Less than 0.1 | 0 |
| 19 | Fisher Scientific | 99+ | Less than 0.1 | 0 |
| 20(Comp.) | AlliedSignal - Hopewell | 98+ | 0.30 | 2.24 |

The ammonium sulfate samples containing less than about 0.2 Wt % water insoluble carbonaceous impurities yielded stable suspensions of the invention.

COMPARATIVE EXAMPLES 21–23

The effect of particle size distribution on the materials used in Examples 17–19. is determined by comparison of the results of grinding the materials with a mortar and pestle versus the SPEX 8000 ball mill used above. A typical size distribution produced by grinding with a mortar and pestle and screening to discard particles retained on a Tyler # 48 sieve is shown in Table V.

TABLE V

| Tyler Sieve No. | Opening size, mm | Wt.% Retained |
|---|---|---|
| 48 | 0.30 | Less than 0.1 |
| 60 | 0.25 | 15 |
| 80 | 0.18 | 16 |
| 100 | 0.15 | 4 |
| 200 | 0.075 | 29 |
| 230 | 0.060 | 27 |
| 400 | 0.030 | 4 |
| Pan | 0 | 4 |

Ammonium sulfate suspensions are prepared according to the procedure described in Examples 17–19. The samples are observed 5 days after mixing. There is a significant amount of free oil on the $5^{th}$ day and the examples are remixed. On the 6$^{th}$ day the free oil is decanted and weighed with the results shown in Table VI.

TABLE VI

| Comparative Example No. | Ammonium sulfate Source | Purity, wt. % | Water-Insoluble Carbonaceous Impurities, Wt % | Free Oil Separated from Suspension, g |
|---|---|---|---|---|
| 21 | AlliedSignal-RP | 98+ | Less than 0.1 | 2.08 |
| 22 | DSM | 95+ | Less than 0.1 | 1.89 |
| 23 | Fisher Scientific | 99+ | Less than 0.1 | 1.56 |

Comparisons of Tables V and VI with Tables III and IV shows that suspension stability with a 29 cp viscosity oil is enhanced by having a particle size distribution with more than 8 wt. % of particles passing a Tyler #230 sieve.

EXAMPLES 24–35

Suspensions of the invention containing varying concentrations of ammonium sulfate between 36.5 wt. % and 72.1 wt. % are prepared in Superla® 5 white mineral oil described in Example 1. Each suspension is prepared by mixing the screened ammonium sulfate described in Example 1 with 5.75 g of mineral oil followed by 0.70 g of Tween® 85 surfactant described in Example 1. No phase separation (presence of free oil) is observed for any suspension after several days. The apparent viscosity of the suspension at 25° C. are characterized by a Brookfield DV-E viscometer with V-4 spindle at 0.3 rpm after stabilizing for 5 minutes. The viscometer reading for each suspension is shown in Table VII in poise and in FIG. 1 as torque in dyne-cm.

TABLE VII

| Example No. | Wt. % Ammonium Sulfate | Apparent Viscosity, poise |
|---|---|---|
| 24 | 36.5 | 340 |
| 25 | 42.2 | 160 |
| 26 | 46.9 | 880 |
| 27 | 51.0 | 600 |
| 28 | 54.4 | 100 |
| 29 | 57.4 | 248 |
| 30 | 60.1 | 640 |
| 31 | 62.4 | 1,740 |
| 32 | 64.5 | 3,760 |
| 33 | 68.0 | 10,620 |
| 34 | 69.5 | 15,260 |
| 35 | 72.1 | 1,738 |

The apparent viscosity of the suspensions increase steeply for this ammonium sulfate at about 68 wt. % solids. The measurement at 72.1 wt. % ammonium sulfate is evidently an artifact, possibly reflecting formation of a low solids boundary layer in the vicinity of the spindle and is not reflective of the flowability of the suspension. Generally, lower viscosity suspensions are more useful for agricultural purposes.

Comparative Examples 36–38 and Examples 39–43

The effect of ammonium sulfate particle size on suspension viscosity is measured at a constant concentration of 58.9 wt. % in a mineral oil of 29 cp viscosity at 40° C. Size fractions of the ammonium sulfate described in example I are separated and mixed with 36.6 wt. % of Superla® 5 white mineral oil described in Example 1 and 4.4 wt. % of Tween® 85 surfactant described in Example 1. The viscometer torque readings for the mixtures at 25° C. and the free oil contents are measured after two days as described above. The measurements are shown in Table VIII.

TABLE VIII

| Example or Comparative Example No. | Passing/Retained Tyler Sieve No. | Viscometer Torque, dyne-cm | Free Oil, Wt. % |
|---|---|---|---|
| 36 (Comp.) | −48/+60 | 27 | 15 |
| 37 (Comp.) | −60/+80 | 32 | 9 |
| 38 (Comp.) | −80/+100 | 29 | 6 |
| 39 | −100/+200 | 24 | 1 |
| 40 | −200/+230 | 30 | 1 |
| 41 | −230/+400 | 34 | 0 |
| 42 | −400/+pan | 247 | 0 |
| 43 | −48/+pan | 113 | 0 |

It is seen that stable ammonium sulfate suspensions are formed with oil of 29 cp viscosity when the suspension contains particles passing a Tyler #100 sieve. Suspensions of the highest stability are formed when the suspension contains particles passing a Tyler #230 sieve

EXAMPLES 44–49

The effects of ammonium sulfate particle size on suspension stability and viscosity are measured at a constant concentration of 58.9 wt. % in a heavier mineral oil having a 40° C. viscosity of 115 cp. Size fractions of the ammonium sulfate described in Example I are separated and mixed with 36.6 wt. % of Superla® 18 white mineral oil having a viscosity of at least about 115 centipoises at 25° C. and 4.4 wt. % of Tween® 85 surfactant described in Example 1. The viscometer torque readings for the mixtures at 25° C. and the free oil contents are measured after five days as described above. The measurements are shown in Table IX.

TABLE IX

| Example or Comparative Example No. | Passing/Retained Tyler Sieve No. | Viscometer Torque, dyne-cm | Free Oil, Wt. % |
|---|---|---|---|
| 44 | −48/+60 | 230 | 15 |
| 45 | −60/+80 | 220 | 2 |
| 46 | −80/+100 | 230 | 1 |
| 47 | −100/+200 | 240 | 0 |
| 48 | −200/+230 | 310 | 0 |
| 49 | −230/+400 | 330 | 0 |

A stable suspension of each ammonium sulfate particle size Tyler #48 screen is formed in oil of 115 cp viscosity.

EXAMPLES 50–57

Ammonium sulfate suspensions of the invention are prepared using the several different non-ionic surfactants described in Table X below. The suspensions are prepared using 9.25 g of the screened ammonium sulfate described in Example 1, 5.75 g of Superla® 5 mineral oil and 0.70 g of the surfactant. Each of the suspensions is stable against phase separation.

To test the rapidity of their dispersion and dissolution in water, a given amount of a suspension is introduced into 60 ml of tap water in a 100 ml beaker with a ⅜ inch by 1.5 inch long magnetic stirring bar turning at a constant but moderate speed. The suspension is rapidly introduced into the water by placing 0.16 g on a piece of wax film (5 mm by 5 mm by 0.127 mm thick) and dropping it into the stirred water.

Several events must occur when the suspension is introduced into water. First the suspension must breakup and the ammonium sulfate dissolve quickly. Second, the oil must be dispersed so that it forms a milky dispersion in the water and not collect on top as a layer.

The time required for dissolution of the ammonium sulfate in water is measured for three portions of each sample and the average is reported below. The deviation in measurements is about ±20%.

TABLE X

| Example No. | Surfactant Composition | HLB Rating | Solution Appearance | Average Time For Ammonium Sulfate To Dissolve, Sec |
|---|---|---|---|---|
| 50 | POE (4) sorbitan monostearate | 9.6 | Clear with oil on top | 1200 |
| 51 | POE(20) sorbitan monostearate | 14.9 | Clear | 159 |
| 52 | POE(20) sorbitan tristearate | 10.5 | Opaque with milky oil layer | 539 |
| 53 | POE(5) sorbitan monooleate | 10.0 | Clear with milky oil layer | 93 |
| 54 | POE(20) sorbitan monooleate | 15.0 | Clear | 165 |
| 55 | POE(10) sorbitan trioleate | 10 | Opaque | 75 |
| 56 | POE(20) sorbitan trioleate | 11.0 | Very opaque | 35 |
| 57 | POE(30) sorbitan trioleate | 15 | Very opaque | 80 |

*POE(n) - poly(ethylene oxide) n mers in length

The dispersion of a suspension is most complete when the surfactant is a polyethylene oxide sorbitan trioleate with between 10 and 30 ethylene oxide mers. The solution of an ammonium sulfate suspension of the invention is most rapid when the suspension is prepared with polyethylene oxide (20) sorbitan trioleate. Polyethylene oxide (20) sorbitan trioleate is commercially available from Uniqema under the trade name Tween® 85 and from other manufacturers as well.

EXAMPLE 58 AND COMPARATIVE EXAMPLE 59

Two suspensions are prepared in Superla® 5 mineral oil containing 58.9 wt. % of the ammonium sulfate described in Example 1 and using the procedure of Example 1 except that one of the suspensions does not contain Tween® 85. Suspension viscosity measurements were made at 25° C. using a Brookfield DV-E viscometer with a LV-4 spindle at 0.3 rpm after stabilizing for 3 minutes. The results are as follows in Table

TABLE XI

| Example No. | Tween ® 85 | Readily Dispersible in Water | Viscometer Torque, dyne-cm |
|---|---|---|---|
| 58 | present | Yes | 4 |
| 59 (Comp.) | absent | No | 537 |

Surprisingly, the presence of Tween® 85 surfactant, necessary for ready dispersibility of the suspension in water, also markedly reduces the viscosity of the suspension.

EXAMPLE 60

A suspension of the invention is prepared containing 58.9 wt. % of the ammonium sulfate described in Example 1, 36.6 wt. % of corn oil having a viscosity of 200 cp at 25° C. and 4.4 wt. % of Tween® 85 surfactant. The suspension is stable showing no phase separation in 48 hours.

EXAMPLE 61

A suspension of the invention is prepared containing 58.9 wt. % of the ammonium sulfate described in Example 1, 36.6 wt. % of soybean oil having a viscosity of 78 cp at 25° C., and 4.4 wt. % of Tween(g) 85 surfactant described in Example 1. The suspension is stable showing no phase separation in 48 hours.

EXAMPLE 62

Reagent grade ammonium sulfate of 99+ wt % purity, containing less than 0.1 wt. % water insoluble impurities is milled in a SPEX ball mill and screened to remove substantially all particles retained on a Tyler #48 sieve. The sieved material is further screened to isolate the following particle size fractions: a) −48/+200 and b) −200/+400. These particle size fractions are combined to create blends in the proportions shown below in Table XII. Each blend is divided into two portions. The first portion of each particle size blend is mixed with the Superla® 5 mineral oil described in Example 1 and the Tween® 85 surfactant described in Example 1 to create suspensions containing 60.8 wt. % ammonium sulfate, 34.6 wt % mineral oil and 4.6 wt % surfactant. The second portion of each particle size blend is mixed with Rhodimet® AT-88 followed by evaporation to dryness at 100° C. The dried ammonium sulfate/AT-88 is mixed with Superla® 5 mineral oil and Tween® 85 to create suspensions containing 60.1 wt % ammonium sulfate, 34.2 wt % mineral oil, 4.6 wt % surfactant and 1.1 wt. % methylthio-α-hydroxybutyric acid (MTHBA).

The several suspensions are examined after two days at room temperature for the presence of free oil and their apparent viscosities at 25° C. .measured with a Brookfield DV-E viscometer with LV-4 spindle at 2.5 RPM after stabilizing for 5 minutes. The results are shown in Table XII.

TABLE XII

| Wt. % in Particle Size Fraction | | Apparent Viscosity, poise | | Free Oil, wt. % | |
|---|---|---|---|---|---|
| −48/+200 | 200/+400 | No MTHBA | With MTHBA | No MTHBA | With MTHBA |
| 100 | 0 | 1090 | 110 | 5.0 | 1.0 |
| 90 | 10 | 1725 | 120 | 6.3 | 4.0 |
| 80 | 20 | 1615 | 154 | 6.9 | 1.0 |

It will be seen that 1.1 wt. % of MTHBA increases the stability and markedly decreases the apparent viscosity of ammonium sulfate-oil suspensions.

Comparative Examples 63–71 and Examples 72–75

The effectiveness of an ammonium sulfate suspension of the invention as a herbicidal adjuvant is determined by Agribiology Research, Inc., Memphis, Tenn. an independent company specializing in such agronomic evaluations. Tests are conducted in a greenhouse using small pots containing three different weed species known as difficult-to-kill weeds. Difficult weeds are those that are resistant to herbicides at commonly used dosage rates. Morning Glory, Velvet Leaf, and Johnson Grass are typical of the difficult-to-kill weeds.

Comparison is made between several treatments as follows:
1. no treatment,
2. an ammonium sulfate suspension of invention alone (no herbicide)
3. herbicide alone
4. herbicide plus a commercial oil adjuvant
5. herbicide plus ammonium sulfate added as solid
6. herbicide plus an ammonium sulfate suspension of the invention The suspension of the invention consists of 57.9 wt. % ammonium sulfate, 37.4 wt. % Superla® 5 mineral oil described in Example 1, and 4.7wt. % Tween® 85 surfactant described in Example 1. All spray solutions except the first two listed above contain 0.938 vol. % of Monsanto Rodeo® brand glyphosate herbicide (isopropylamine salt of N-(phosphonomethyl)glycine). This dose is equivalent to 12 U.S. fluid ounces per acre of glyphosate herbicide. It is common practice and recommended by adjuvant manufacturers to mix the adjuvants in the water before adding the glyphosate. That procedure is followed in these experiments.

The plants are sprayed only once at about the 7 inch stage in a cabinet with a flat fan nozzle from a height of about 18 inches and at a speed of about 4 mph and volume of 10 gallons per acre. Fourteen days after the treatment the plants are cut off at ground level and weighed. This is called fresh weight. The weight of plant tissue killed by the herbicide is very small when dry compared to the green tissue (new growth). Therefore the recorded fresh weight is effectively the measure of new growth after treatment.

In Table XIII below, the designation "AS" means ammonium sulfate added as solid. The designation "Oil" means Agridex®, a common crop oil used as adjuvant and supplied by Helena Corporation of Memphis, Tenn. The term, "Suspension", designates the suspension of this invention. Table XIII lists the results when these different additives are used with the glyphosate. The fresh weight data is the average obtained from three pots for each weed species.

TABLE XIII

| | | | Fresh Weight, g/pot | | |
| --- | --- | --- | --- | --- | --- |
| Example No. | Weed Treatment | Adjuvant Dose, lb/acre | Velvet Leaf | Morning Glory | Johnson Grass |
| 63(Comp.) | No Treatment | 0 | 2.48 | 2.90 | 1.79 |
| 64(Comp.) | Suspension Alone | 2.81 | 2.24 | 2.75 | 2.60 |
| 65(Comp.) | Glyphosate Alone | 0 | 1.44 | 1.43 | 0.96 |
| 66(Comp.) | Glyphosate + Oil | 0.26 | 1.46 | 0.22 | 0.65 |
| 67(Comp.) | Glyphosate + Oil | 0.51 | 1.25 | 0.07 | 0.61 |
| 68(Comp.) | Glyphosate + AS | 0.21 | 0.73 | 0.43 | 0.46 |
| 69(Comp.) | Glyphosate + AS | 0.43 | 0.57 | 0.38 | 0.46 |
| 70(Comp.) | Glyphosate + AS | 0.85 | 0.38 | 0.26 | 0.50 |
| 71(Comp.) | Glyphosate + AS | 1.7 | 0.20 | 0.06 | 0.65 |
| 72 | Glyphosate + Suspension | 0.35 | 0.53 | 0.19 | 0.36 |
| 73 | Glyphosate + Suspension | 0.7 | 0.29 | 0.0 | 0.33 |
| 74 | Glyphosate + Suspension | 1.41 | 0.37 | 0.20 | 0.66 |
| 75 | Glyphosate + Suspension | 2.81 | 0.31 | 0.03 | 1.05 |

TABLE XIII-continued

| | | | Fresh Weight, g/pot | | |
| --- | --- | --- | --- | --- | --- |

The data for adjuvant doses less than 1 lb/acre are plotted in FIGS. 2A, 2B and 2C. In each plot, the diamonds are the data for glyphosate+oil, the squares are for glyphosate+AS and the triangles are for glyphose+suspension. It is seen that at doses less than 1 lb/acre, the glyphosate plus the suspension of the invention (triangles) produces either the same, or substantially more kill of these difficult weeds than does either the commercial oil, or ammonium sulfate added as solid.

The data shows a surprising and synergistic performance of the combination of constituents in the suspension of the invention. This is all the more surprising in view of the aforementioned De Ruiter et al. prior art publication indicating that mineral oil decreased the activity of glyphosate.

Herbicide manufacturers usually recommend applying double the dose of herbicide when difficult weeds are present. However, from an environmental point of view it is more desirable to use less herbicide and an adjuvant to obtain the same effect. The suspensions of the invention meet that need.

Comparative Example 76 and Examples 77–84

Suspensions of the invention containing ammonium sulfate and solid herbicides are prepared. The herbicides listed in Table XIV below are screened to substantially remove particles not passable through a Tyler #48 sieve. Where necessary, the herbicides were ground with a motor and pestle prior to screening.

The herbicides are obtained from Aldrich Co. except for the dimethylarsinic acid which is obtained from Sigma Chemical Co. The ammonium sulfate is the same screened material described in Example 1. The mixtures are prepared by the same procedure described in Example 1 except that the ammonium sulfate and dry herbicide are added as a dry mixture. Mineral oil (Superla® 5 described in Example 1) in the amount of 5.75 g and 0.70 g of Tween® 85 surfactant described in Example 1 are used in all preparations. The compositions are typical of commercial herbicide preparations.

The mixtures are examined 4 days after preparation to determine appearance, stability, and general physical characteristics.

TABLE XIV

| Ex. No. | Herbicide | Weight Used, g Herbicide | Ammonium sulfate | Observations |
|---|---|---|---|---|
| 76 Comp. | 3-amino-1,2,4-triazole | 2.78 | 6.48 | Dark liquid, phase separated |
| 77 | Sodium trichloroacetate | 2.78 | 6.48 | Stable suspension, High viscosity |
| 78 | Sodium trichloroacetate | 3.32 | 8.14 | Stable suspension, High viscosity |
| 79 | 2,4-dichlorophenoxy acetic acid | 2.78 | 6.48 | Stable suspension |
| 80 | 2,4-dichlorophenoxy acetic acid | 3.32 | 8.14 | Stable suspension, High viscosity |
| 81 | 2-(2,4-dichlorophenoxy) propionic acid | 2.78 | 6.48 | Stable suspension |
| 82 | 2-(2,4-dichlorophenoxy) propionic acid | 3.32 | 8.14 | Stable suspension, High viscosity |
| 83 | dimethylarsinic acid | 3.32 | 8.14 | Stable suspension |
| 84 | n-(phosphomethyl) glysine isopropyl salt | 3.32 | 8.14 | Stable suspension |

Apparently the triazole reacts with one of the other ingredients. No free oil is found in the other mixtures. Both suspensions incorporating sodium trichloroacetate have unusually high viscosity. The suspension containing the higher concentration of 2-(2,4-dichlorophenoxy)propionic acid (Example 77) also has a high viscosity. Otherwise, all the samples have the appearance, stability, and general physical characteristics of suspensions containing only ammonium sulfate.

Comparative Example 85

A test is made of the feasibility of using water-soluble packaging with of a suspension of the invention. Most water soluble packaging films consist of polyvinyl alcohol-acetate film. A comparison is made with solid ammonium sulfate.

One gram of solid ammonium sulfate crystals (0.9 mm average size) is sealed in a bag of polyvinyl alcohol-acetate film (PVA film) of about 0.05 mm thickness, approximately 25.4 mm by 25.4 mm. The bag is prepared and sealed using a heat sealer. A 250 ml beaker is filled with about 125 ml of tap water and a magnetic stir bar was used to gently stir the water. The bag is dropped in while the water is being stirred in a constant manner.

After about 60 seconds the bag breaks open and some of the crystals dissolved. Pieces of the bag eventually break off and continued to swirl around the beaker. The film is sticky. About one-half of the remaining crystals are enveloped by the bag as it folds over on itself. This prevents the remaining crystals from being exposed to the water. Fragments of the bag and some crystals remain after 30 minutes of stirring. The fragments and insoluble materials would plug spray nozzles and are unacceptable for commercial use. This experiment demonstrates that PVA film could not be used for packaging solid particles of ammonium sulfate. Similar results and conclusions are reached with aqueous solutions of ammonium sulfate.

EXAMPLE 86

One gram of an ammonium sulfate suspension of the invention prepared in the manner of Example 1 is sealed in a bag of polyvinyl alcohol-acetate film (PVA film) of about 0.05 mm thickness, approximately 25.4 mm by 25.4 mm. The bag is dropped into a stirred beaker of water as in Comparative Example 81.

The bag containing the ammonium sulfate suspension of the invention breaks open and releases its contents and all of the film dissolves in less than 15 minutes. This experiment indicates that the suspensions of the invention can be packaged in water-soluble PVA film. This provides a distinct advantage in ease of use as the customer can drop the bag of pre-weighed chemicals in water without handling or measuring.

What is claimed is:

1. A stable ammonium sulfate suspension readily dispersible in water comprising:
   a. ammonium sulfate particles at least about 99 wt. % passable through a Tyler #48 sieve;
   b. a non-ionic surfactant having an HLB rating between about 10 and about 15; and
   c. non-polar oil having a viscosity of at least about 5 centipoises at 40° C.

2. The ammonium sulfate suspension of claim 1, wherein the ammonium sulfate particles are at least about 99.9 wt. % passable through a Tyler #48 sieve.

3. The ammonium sulfate suspension of claim 1, wherein the ammonium sulfate is of at least about 95 wt. % purity and contains less than about 0.2 wt. % of water insoluble organic or carbonaceous impurities.

4. The ammonium sulfate suspension of claim 1, wherein the ammonium sulfate concentration is from about 30 wt. % to about 70 wt. %.

5. The ammonium sulfate suspension of claim 1, wherein the ammonium sulfate concentration is from about 40 wt. % to about 70 wt. %.

6. The ammonium sulfate suspension of claim 1, wherein the ammonium sulfate concentration is from about 50 wt. % to about 70 wt. %.

7. The ammonium sulfate suspension of claim 1, wherein at least about 8 wt. % of the ammonium sulfate particles are passable through a Tyler #230 sieve.

8. The ammonium sulfate suspension of claim 1, wherein about 20 wt. % to about 60 wt. % of the ammonium sulfate particles are passable through a Tyler #230 sieve.

9. The ammonium sulfate suspension of claim 1, wherein the non-ionic surfactant is a polyethylene oxide-sorbitan fatty acid ester.

10. The ammonium sulfate suspension of claim 1, wherein the non-ionic surfactant is a polyethylene oxide sorbitan trioleate with between about 10 and about 30 ethylene oxide mers.

11. The ammonium sulfate suspension of claim 1, wherein the non-ionic surfactant is polyethylene oxide (20) sorbitan trioleate.

12. The ammonium sulfate suspension of claim 1, wherein the non-ionic surfactant concentration is between about 3 wt. % to about 8 wt. %.

13. The ammonium sulfate suspension of claim 1, wherein the non-ionic surfactant concentration is between about 4 wt. % to about 5 wt. %.

14. The ammonium sulfate suspension of claim 1, wherein the non-polar oil comprises one or more of petroleum oils, polyoxyethylated castor oil, cod liver oil, epoxidized linseed oil, fish oil, oils derived from plants and animals, mineral oil, sperm oil, tall oil, wintergreen oil, and rapeseed oil.

15. The ammonium sulfate suspension of claim 1, wherein the non-polar oil is at least one member of the group consisting of cotton seed oil, corn oil, coconut oil, soybean oil, epoxidized soybean oil and a hydrocarbon oil.

16. The ammonium sulfate suspension of claim 1, wherein the non-polar oil is a white mineral oil having a viscosity at 40° C. from about 10 centipoises to about 220 centipoises.

17. The ammonium sulfate suspension of claim 1 additionally containing methylthio-α-hydroxybutyric acid.

18. The ammonium sulfate suspension of claim 1 additionally containing a solid herbicide.

19. The ammonium sulfate suspension of claim 1 contained in a water-soluble package.

20. The ammonium sulfate suspension of claim 18 wherein the water-package is composed of polyvinyl alcohol-acetate.

* * * * *